(12) United States Patent
Martin et al.

(10) Patent No.: US 8,768,112 B2
(45) Date of Patent: Jul. 1, 2014

(54) SYSTEM HAVING FIBER OPTIC PURITY SENSOR

(75) Inventors: Matthew Robert Martin, Schenectady, NY (US); Anthony James George, Clifton Park, NY (US); Jeffrey James Andritz, Altamont, NY (US); James Daniel Antalek, Valatie, NY (US); James Thomas Clark, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 775 days.

(21) Appl. No.: 12/910,522

(22) Filed: Oct. 22, 2010

(65) Prior Publication Data

US 2012/0098360 A1   Apr. 26, 2012

(51) Int. Cl.
*G02B 6/00* (2006.01)

(52) U.S. Cl.
USPC .......................................................... 385/12

(58) Field of Classification Search
None
See application file for complete search history.

(56) References Cited

U.S. PATENT DOCUMENTS

| | | | | |
|---|---|---|---|---|
| 2,988,656 A | * | 6/1961 | Grobel | 310/53 |
| 5,179,523 A | * | 1/1993 | Johnson | 702/24 |
| 5,280,172 A | * | 1/1994 | Di Bin et al. | 250/227.21 |
| 6,519,041 B1 | * | 2/2003 | Berthold | 356/477 |
| 7,151,872 B1 | * | 12/2006 | Xia et al. | 385/37 |
| 7,489,835 B1 | * | 2/2009 | Xia et al. | 385/12 |
| 7,549,803 B2 | * | 6/2009 | Thompson et al. | 385/88 |
| 8,128,875 B2 | | 3/2012 | Andritz et al. | |
| 8,467,977 B2 | | 6/2013 | Xia et al. | |
| 2004/0173004 A1 | | 9/2004 | Eblen, Jr. et al. | |
| 2008/0218758 A1 | * | 9/2008 | Xia et al. | 356/437 |
| 2012/0026482 A1 | * | 2/2012 | Dailey | 356/43 |

FOREIGN PATENT DOCUMENTS

| | | |
|---|---|---|
| GB | 2478190 A | 8/2011 |
| GB | 2478829 A | 9/2011 |
| WO | 91/06852 A1 | 5/1991 |
| WO | 2006/057984 A2 | 6/2006 |
| WO | 2008/136870 A2 | 11/2008 |

OTHER PUBLICATIONS

Great Britain Search Report issued in connection with GB Patent Application No. 1118048.6, Jan. 18, 2012.
"Generator Products," http://www.gepower.com/prod_serv/products/generators/en/downloads/generators.pdf (16 pages), May 2005.
Wolff, David E., "Hydrogen for Generator Cooling—The Pressure, Purity and Dewpoint Difference," http://www.protonenergy.com/backend/arc_contenido/archivo117.pdf (26 pages), Last accessed Jul. 22, 2010.
http://www.control.com/thread/1267097548, last accessed Dec. 10, 2010 (8 pages).
Vandervort, Christian L., et al, "GE Generator Technology Update," http://www.gepower.com/prod_serv/products/tech_docs/en/downloads/ger4203.pdf (20 pages), Apr. 2001.

(Continued)

*Primary Examiner* — Michelle R Connelly
(74) *Attorney, Agent, or Firm* — Fletcher Yoder P.C.

(57) ABSTRACT

A system includes an electrical generator comprising a stator, a rotor, and a gas coolant path through an interior of the electrical generator and at least one fiber optic purity sensor configured to sense a gas purity of a flow of a gas coolant through the gas coolant path.

16 Claims, 5 Drawing Sheets

(56) References Cited

OTHER PUBLICATIONS

"Life Extension Services (LES) Generator Cooling Gas Purity Thermal Gas Analyzers," http://www.gepower.com/prod_serv/products/generators/en/downloads/gen_gas_analyser.pdf (3 pages), Last accessed Dec. 10, 2010.

http://www3.toshiba.co.jp/power/english/thermal/products/generators/hydrogen.htm last accessed Dec. 10, 2010 (2 pages).

http://www.mhi.co.jp/en/products/detail/turbine_generator_system.html last accessed Dec. 10, 2010 (2 pages).

U.S. Appl. No. 12/754,391, filed Apr. 5, 2010, Benjamin Campbell Steinhaus.

U.S. Appl. No. 12/725,664, filed Mar. 17, 2010, Hua Xia.

\* cited by examiner

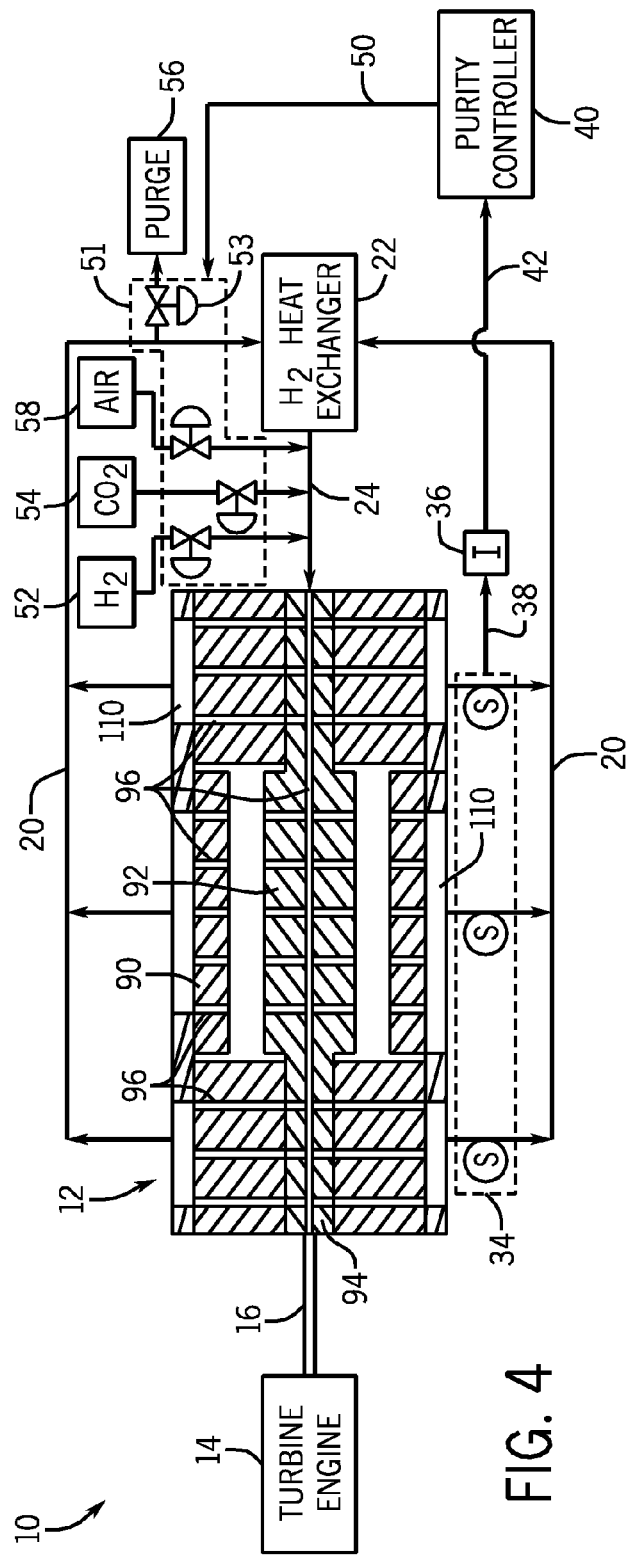

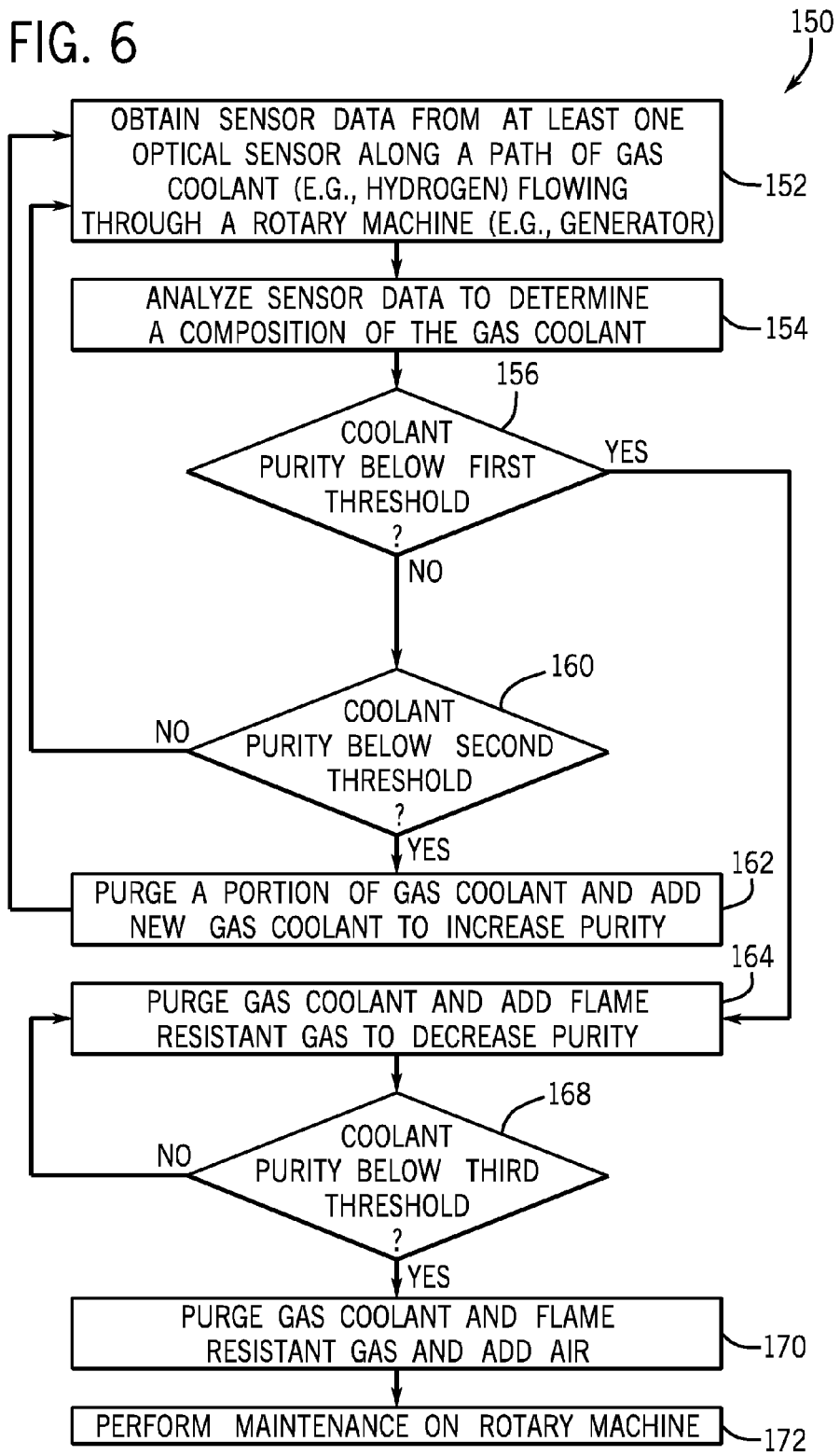

SYSTEM HAVING FIBER OPTIC PURITY SENSOR

BACKGROUND OF THE INVENTION

The subject matter disclosed herein relates to systems for purity detection and, more particularly, to systems using fiber optic purity sensors.

Gases are used in a wide range of applications covering many industries, such as fuel cells, transportation, and power generation. For example, hydrogen may be used as a coolant in electrical equipment, such as electrical generators. Other gases, such as carbon dioxide and air, may also be used in electrical generators. A purity requirement of hydrogen varies depending on the application. For example, electrical generators may require high purity hydrogen to avoid creating combustible gas mixtures. Existing hydrogen purity monitoring instruments are typically based on thermal conductivity detection (TCD). TCD is a general-purpose gas analysis method with non-specific and nondestructive characteristics and may be less sensitive than flame ionization detection methods. The resolution and accuracy of TCD may be limited. Other methods for monitoring hydrogen purity include the use of gas density and differential pressure based measurements. However, these methods are subject to ambient and gas temperature-induced variations. Therefore, there is a need for an improved purity measurement sensor and system to address one or more of the aforementioned issues.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes an electrical generator comprising a stator, a rotor, and a gas coolant path through an interior of the electrical generator and at least one fiber optic purity sensor configured to sense a gas purity of a flow of a gas coolant through the gas coolant path.

In a second embodiment, a system includes a gas purity control system that includes a purity controller, and at least one fiber optic purity sensor configured to sense a gas purity.

In a third embodiment, a system includes at least one fiber optic purity sensor configured to sense a gas purity of a gas coolant. The at least one fiber optic purity sensor includes a fiber core, a refractive index periodic modulated grating structure positioned about the fiber core, a fiber cladding positioned around the refractive index periodic modulated grating structure, and a multilayered sensing film positioned about the fiber cladding. The multilayered sensing film comprises a modulated structure of multiple high refractive index and low refractive index material layers. The system also includes a purity controller configured to initiate a control function to increase the gas purity if a sensed level is below a threshold level of the gas purity.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 4 is a partial cross-sectional view of an electrical generator system incorporating a fiber optic purity sensor according to an embodiment;

FIG. 5 is a schematic representation of a fiber optic purity sensor in accordance with an embodiment of the present invention; and FIG. 6 is a flow chart of a process for operating an electrical generator incorporating a fiber optic purity sensor according to an embodiment.

DETAILED DESCRIPTION OF THE INVENTION

Figure 1:
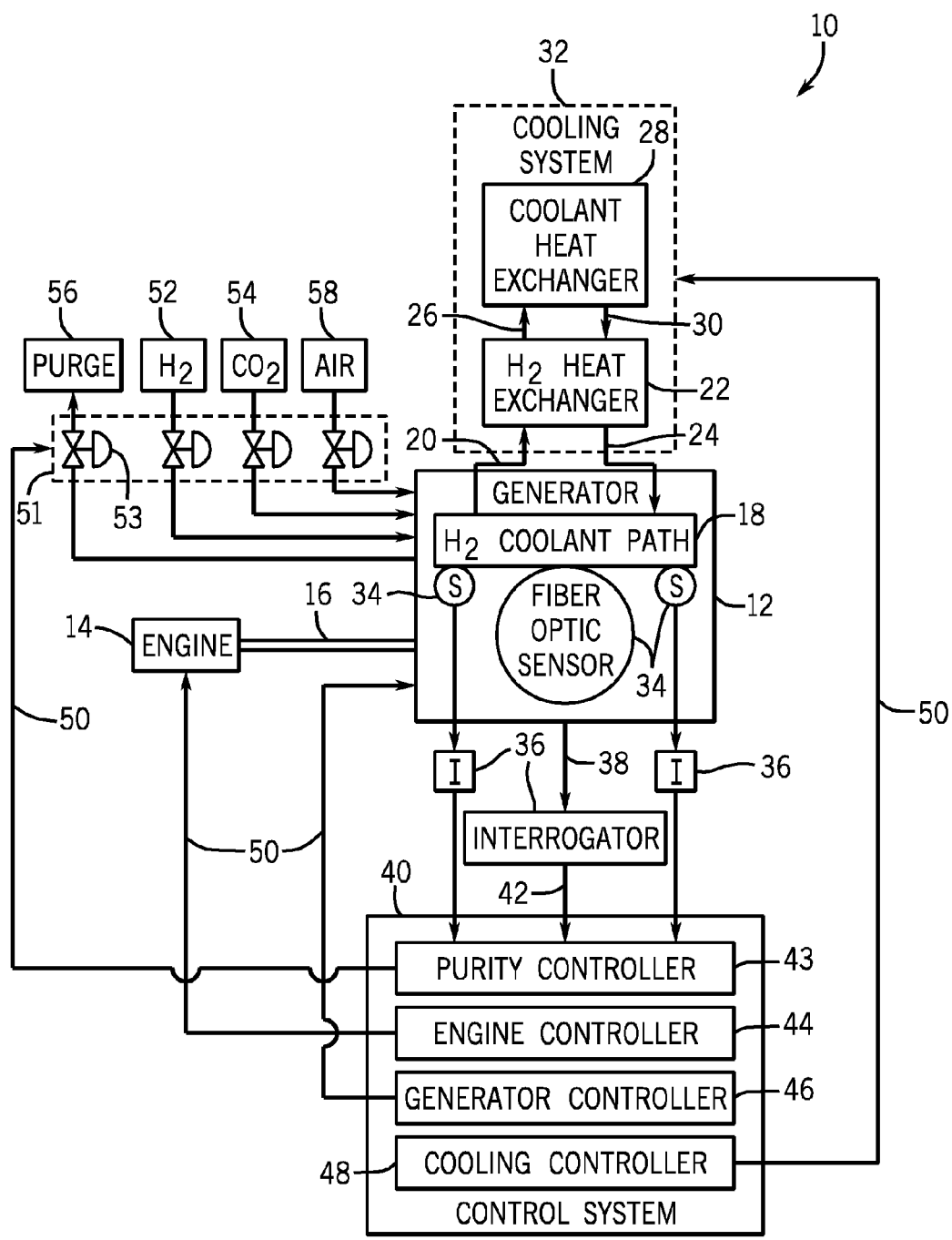
FIG. 1 is a block diagram of an electrical generator system incorporating a fiber optic purity sensor according to an embodiment.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed in detail below, some of the disclosed embodiments include systems directed toward electrical generators that include a stator, a rotor, and a gas coolant path through an interior of the electrical generator. More generally, other embodiments include any rotary machine, such as turbines, combustion engines, electrical generators, electric motors, and so forth. The use of hydrogen as a coolant for electrical equipment, such as electrical generators, offers several advantages over other gases, as discussed below. Other gases may also be used in electrical generators. The disclosed systems also include at least one fiber optic purity sensor, which may be configured to sense a gas purity of a flow of a gas coolant through a gas coolant path. Gas purity monitoring may be a requirement of industry standards, such as Institute of Electrical and Electronics Engineers (IEEE) standards. As described in detail below, the fiber optic purity sensor may include several components that work together to enable the sensor to sense the gas purity of the gas coolant. For example, the fiber optic purity sensor may include various coatings, or sensing layers, each of which may enable the sensor to detect different gas purity levels. In certain embodiments, the fiber optic purity sensor may include a first coating configured to enable detection of a hydrogen level in air, a second coating configured to enable detection of a hydrogen level in carbon dioxide ($CO_2$), and a third coating configured to enable detection of a $CO_2$ level in air. The use of fiber optic purity sensors in electrical generators may facilitate the addition of other fiber optic sensors, such as pressure, temperature, and flow rate sensors. Such fiber optic sensors may be able to all share the same interrogator system, thereby potentially reducing capital, maintenance, and operating expenses. As described in detail below, the interrogator system translates optical signals into values of the monitored parameters. Further, compared to other sensors, fiber optic sensors offer several advantages, such as small size, no requirement for electrical power, potential for multiplexing, resistance to electrical and/or magnetic fields, suitability for high temperatures and/or pressures, high accuracy, and so forth.

Some of the disclosed embodiments are directed toward gas purity control systems that include a purity controller, and at least one fiber optic purity sensor configured to sense a gas purity. The purity controller may be configured to initiate a control function to increase the gas purity if a sensed level is below a threshold level of the gas purity. In certain embodiments, the threshold level of the gas purity may be based on avoiding a combustible mixture inside a gas cooling system. Examples of control functions that may be initiated by the purity controller include venting off a portion of low-purity gas and/or adding additional high-purity gas. Thus, by using the accurate feedback from the fiber optic purity sensor, the cooling controller may help to maintain the gas cooling system within a desired operating window.

FIG. 1 is a block diagram of an electrical generator system 10 according to an embodiment. The electrical generator system 10 may include an electrical generator 12, which is a device that converts mechanical energy to electrical energy. The source of the mechanical energy may be an engine 14 that is coupled to the electrical generator 12 via a drive shaft 16. Examples of the engine 14 include, but are not limited to, steam turbine engines and gas turbine engines. During operation, the electrical generator 12 may generate heat, which may be removed using a coolant. Examples of coolants that may be used in the electrical generator 12 include, but not limited to, air, water, hydrogen, helium, and so forth. In the illustrated embodiment, the electrical generator 12 includes a hydrogen coolant path 18. The hydrogen coolant path 18 may be disposed inside the electrical generator 12, near an external surface of the electrical generator 12, or wherever heat may be removed. Thus, the hydrogen coolant path 18 may include passages, conduits, or pipes to carry hydrogen through the electrical generator 12. Hydrogen offers several advantages compared to other coolants that may be used for the electrical generator 12. Specifically, hydrogen has a low density, a high specific heat, and a high thermal conductivity. Because of these properties, electrical generators 12 that use hydrogen as a coolant may be smaller and less expensive than electrical generators 12 that use other coolants, such as air.

After removing heat in the electrical generator 12, warm hydrogen 20 may be directed to a hydrogen heat exchanger 22, such as a shell and tube heat exchanger or a plate heat exchanger, for example. The hydrogen heat exchanger 22 removes heat from the warm hydrogen 20 and returns cool hydrogen 24 to the hydrogen coolant path 18 to be used to remove additional heat from the electrical generator 12. Thus, the hydrogen used in the electrical generator 12 is circulated in essentially a closed loop. The pressure of the hydrogen in the hydrogen coolant path 18 may be greater than approximately 400 kilopascal (kPa), 500 kPa, or 600 kPa. The purity of the hydrogen in the hydrogen coolant path 18 may be very high to help reduce the possibility of corona discharges caused by the presence of oxygen. For example, the purity of the hydrogen in the hydrogen coolant path 18 may be greater than approximately 95 percent, 98 percent, or 99 percent.

A coolant may be used to remove the heat from the hydrogen circulated through the hydrogen heat exchanger 22. The coolant may be a liquid, such as water, refrigerant, heat exchange fluid, or the like. Warm coolant 26 from the hydrogen heat exchanger 22 may be directed to a coolant heat exchanger 28, which may be configured to remove heat from the warm coolant 26. The coolant heat exchanger 28 may be a shell and tube heat exchanger, a plate heat exchanger, or any other suitable type of heat exchanger. Cool coolant 30 may be directed from the coolant heat exchanger 28 to the hydrogen heat exchanger 22, creating essentially a closed loop system. In other embodiments, the coolant heat exchanger 28 may be omitted and an open loop coolant system may be used instead of the closed loop system. For example, the warm coolant 26 may be cooling water that is directed to one portion of a large reservoir, such as a lake or river, and the cool coolant 30 may be cooling water obtained from another portion of the reservoir. Together, the hydrogen heat exchanger 22 and the coolant heat exchanger 28 may be referred to as a hydrogen cooling unit or hydrogen cooling system 32.

Disposed inside the electrical generator 12 may be one or more fiber optic sensors 34, configured to monitor various locations along the hydrogen coolant path 18. The fiber optic sensors 34 may be configured to monitor or detect at least one of the following gas purity levels: a hydrogen level in air, a hydrogen level in $CO_2$, or a $CO_2$ level in air. The fiber optic sensors 34 are described in more detail below. An interrogator 36 may be coupled to the fiber optic sensors 34 and used to determine the gas purity level based on a signal from the fiber optic sensors 34. Specifically, a fiber optic cable 38 may connect the fiber optic sensor 34 and the interrogator 36. The fiber optic sensor 34 sends a fiber optic signal along the fiber optic cable 38 and the signal is then translated into a gas purity reading by the interrogator 36. The gas purity information from the interrogator 36 may be sent to a control system 40 via a signal 42. For example, the signal 42 may be a 4 mA to 20 mA electric signal and transmitted via wire or wirelessly. The control system 40 may be a stand-alone process control system or part of a larger process control system. Examples of technologies that may be used for the control system 40 include, but are not limited to, open or closed loop control, linear or non-linear control, programmable logic controllers (PLCs), distributed control systems (DCSs), model predictive control, statistical process control, or other methods of advanced process control. In addition, the control system 40 may include a purity controller 43, an engine controller 44, a generator controller 46, a cooling controller 48, and so forth. Based on various inputs, the controllers 43, 44, 46, and 48 may send output signals 50 to various components of the electrical generator system 10. For example, the purity controller 43 may receive the signals 42 from the interrogators 36 and send the output signal 50 to a gas control device 51, which may include one or more control valves 53 to control flow rates of gases to and from the electrical generator 12. The engine controller 44 may receive the signals 42 and send the output signal 50 to the engine 14. If the gas purity information is not within a threshold, the engine controller 44 may direct the engine 14 to shutdown. Similarly, the generator controller 46 and the cooling controller 48 may send output signals 50 to the electrical generator 12 and cooling system 32, respectively, based on the gas purity information.

During operation, hydrogen 52 may be supplied to the electrical generator 12 to replace any hydrogen that may have leaked or been removed from the electrical generator 12. In addition, the hydrogen 52 may be supplied to the electrical generator 12 when first placing the electrical generator 12 in service. As described in detail below, the hydrogen 52 may be displaced by $CO_2$ 54 when preparing the electrical generator 12 for maintenance. As a non-combustible gas, the $CO_2$ 54 may be safely combined with the hydrogen 52. The displaced hydrogen 52 is sent to a purge 56. Once all, or substantially all, the hydrogen 52 has been displaced by the $CO_2$ 54, the $CO_2$ 54 may be displaced by air 58. Thus, the $CO_2$ 54 is sent to the purge 56. Once all, or substantially all, the $CO_2$ 54 has been displaced by air 58, the electrical generator 12 may be ready for maintenance.

Figure 2:
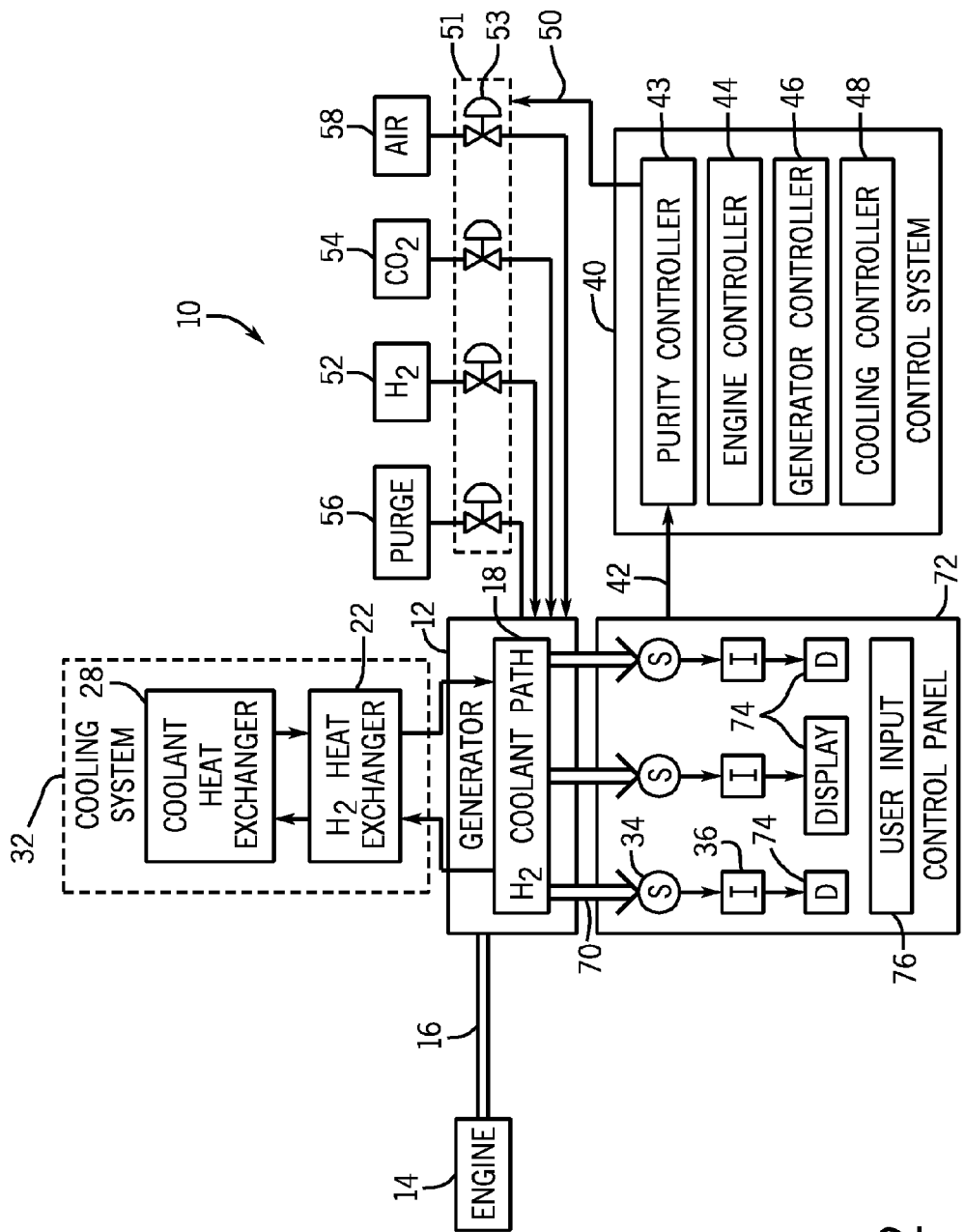
FIG. 2 is a block diagram of an electrical generator system incorporating a fiber optic purity sensor according to an embodiment.

FIG. 2 is a block diagram of another embodiment of an electrical generator system 10. Elements in FIG. 2 in common with those shown in FIG. 1 are labeled with the same reference numerals. In the illustrated embodiment, the fiber optic sensors 34 are not disposed inside the electrical generator 12. Instead, gas sampling tubing or piping 70 may carry gas from the electrical generator 12 to the fiber optic sensors 34, which may be disposed in a control panel 72. Thus, in some embodiments, the hydrogen coolant path 18 may include both an internal portion inside the electrical generator 12 and an external portion that includes the tubing 70, which may also be referred to as a hydrogen coolant line. The tubing 70 may be made from materials such as 304 stainless steel or 316 stainless steel and may have an outside diameter of approximately 3 mm, 6 mm, 9 mm, or 12 mm, for example. The tubing 70 carries a small amount of the gas from inside the electrical generator 12 to the fiber optic sensors 34. As described above, the interrogators 36 determine the gas purity information based on signals from the fiber optic sensors 34. The interrogators 36 may send the gas purity information to one or more displays 74 disposed in the control panel 72. The displays 74 may enable an operator standing near the control panel 72 to observe the gas purity information. The control panel 72 may also include a user input panel 76, which may enable the operator to provide input to the fiber optic sensors 34, interrogators 36, and/or displays 74. For example, the user input panel 76 may enable the operator to change the configuration or settings of any of the components of the control panel 72. Disposing the fiber optic sensors 34 in the control panel 72 may offer several advantages over disposing the fiber optic sensors 34 inside the electrical generator 18. For example, maintenance or replacement of the fiber optic sensors 34 may be easier when disposed in the control panel 72, because the fiber optic sensors 34 are more accessible. Other aspects of the electrical generator system 10 are similar to those described in detail above.

Figure 3:
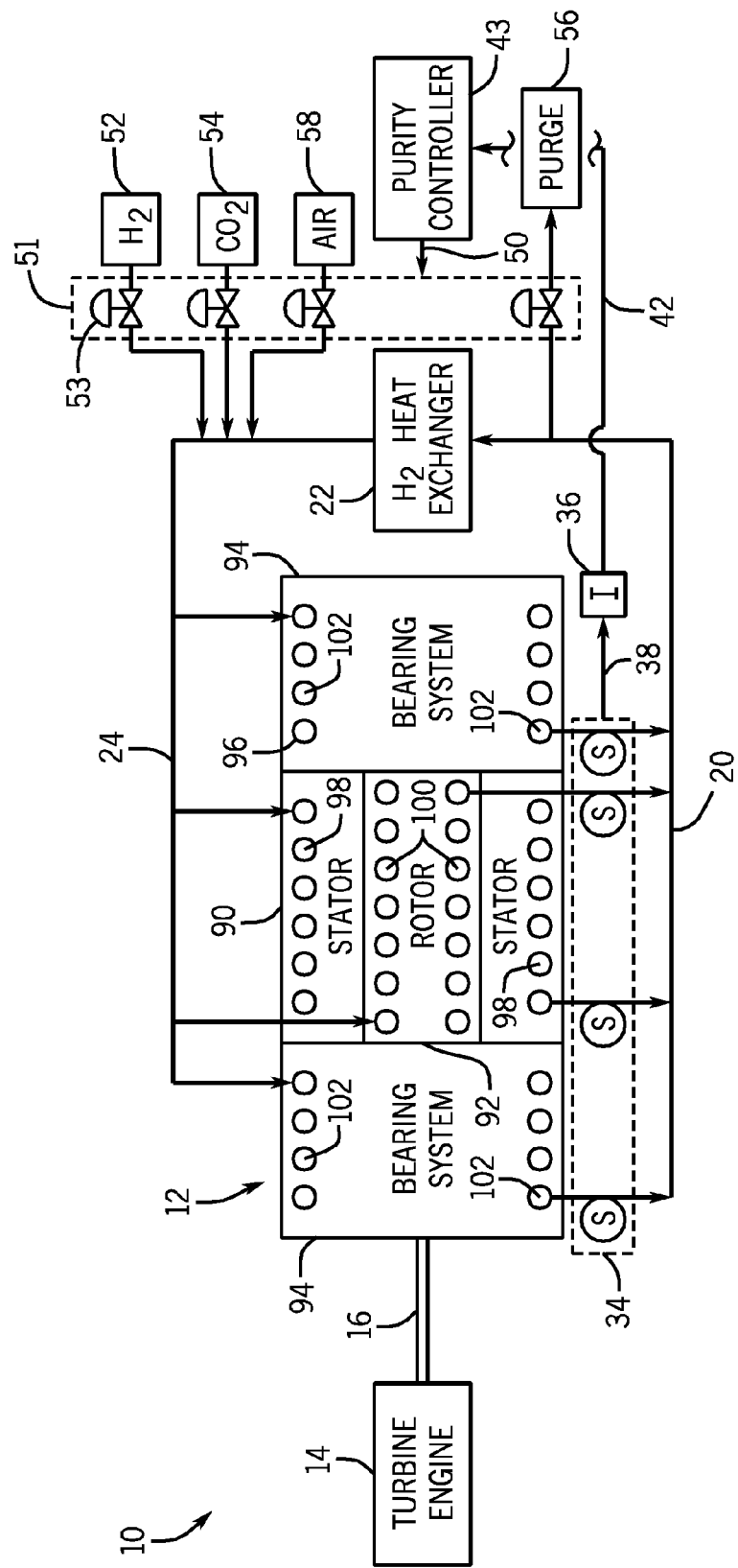
FIG. 3 is a schematic diagram of an electrical generator system incorporating a fiber optic purity sensor according to an embodiment.

FIG. 3 is a schematic diagram of an electrical generator system 10 according to another embodiment. Elements in FIG. 3 in common with those shown in FIG. 1 are labeled with the same reference numerals. The illustrated embodiment shows further details of the electrical generator 12 and the hydrogen coolant path 18. Specifically, the electrical generator 12 may include a stator 90, which is the stationary part of the electrical generator 12, and a rotor 92, which is the rotating part of the electrical generator 12. The stator 90 may be located near the outer circumference of the electrical generator 12 and the rotor 92 may be located near the central axis of the electrical generator 12. Alternatively, the rotor 92 may be located near the outer circumference of the electrical generator 12 and the stator 90 may be located near the central axis of the electrical generator 12. In addition, the electrical generator 12 may include one or more bearing systems 94 to facilitate rotation of the rotor 92. The bearing system 94 may include one or more seals to help prevent leakage of gas into or out of the electrical generator 12.

The stator 90, rotor 92, and/or bearing system 94, may each include one or more coolant passages 96, which may be configured to provide circulation of the coolant through the electrical generator 12. In the illustrated embodiment, the coolant passages 96 may be coils or windings that extend around the components, back and forth along the components, or a combination thereof. In some embodiments, the coolant passages 96 may extend in axial, circumferential, or radial directions in the components. In the illustrated embodiment, the hydrogen coolant path 18 may include a stator coolant path 98 extending through the stator 90, a rotor coolant path 100 extending through the rotor 92, and/or a bearing coolant path 102 extending through the bearing system 94. Specifically, in certain embodiments, the cool hydrogen 24 may enter one end of the stator 90, rotor 92, and/or bearing system 94 and exit an opposite end of these components of the electrical generator 12. In addition, the fiber optic sensors 34 may be disposed throughout the electrical generator 12 to measure the gas purities of the stator 90, rotor 92, and/or bearing system 94. Although shown outside of the electrical generator 12 in FIG. 3, the fiber optic sensors 34 may be disposed inside the electrical generator 12, along the internal portion of the hydrogen coolant path 18, in other embodiments. For example, a stator fiber optic purity sensor 34 may be coupled to the stator coolant path 98, a rotor fiber optic purity sensor 34 may be coupled to the rotor coolant path 100, and/or a bearing fiber optic purity sensor 34 may be coupled to the bearing coolant path 102. More generally, a first fiber optic purity sensor 34 may be configured to sense a first gas purity of a first region of the electrical generator 12, and a second fiber optic purity sensor may be configured to sense a second gas purity of a second region of the electrical generator 12. Other aspects of the electrical generator system 10 are similar to those described in detail above.

FIG. 4 is a partial cross-sectional view of the electrical generator system 10. Elements in FIG. 4 in common with those shown in FIG. 1 and FIG. 3 are labeled with the same reference numerals. In the illustrated embodiment, the cool hydrogen 24 flows through one or more coolant passages 96 disposed throughout the electrical generator 12. For example, in certain embodiments, the cool hydrogen 24 may directed first to the coolant passage 96 located inside and near the central axis of the rotor 92. The cool hydrogen 24 may then be directed radially outward through additional coolant passages 96 to provide cooling for the rest of the rotor 92. In other embodiments, further coolant passages 96 may be disposed in the stator 90 and/or the bearing system 94. After passing through the coolant passages 96, the warm hydrogen 20 may be collected in one or more headers 110 located near the periphery of the electrical generator 12. From the headers 110, the warm hydrogen 20 may return to the hydrogen heat exchanger 22. The use of the headers 110 in certain embodiments may reduce the number of individual lines or conduits to carry the warm hydrogen 20 to the hydrogen heat exchanger 22. Other aspects of the electrical generator system 10 are similar to those described in detail above.

FIG. 5 shows an embodiment of a fiber optic purity sensor 34 that may be used with the electrical generator systems 10 described in detail above. In the illustrated embodiment, the gas purity sensor 34 includes a light source 110, such as tunable, broadband light source, in light communication with a central fiber core 112 that extends along an axis 114 and includes a refractive index periodic modulated grating. A refractive index periodic modulated fiber grating may be made from a process that uses an ultraviolet (UV) light and a phase mask to form an interference pattern, which then illuminates onto the fiber core 112. After the fiber core 112 has been exposed for a certain time, a periodic refractive index pattern forms inside the fiber core 112. The brightly illuminated areas have a higher refractive index than dark areas not illuminated by UV light, such that a periodic modulation is formed. Such a refractive index periodic modulated grating structure may effectively reflect a small portion of a broadband light at a wavelength that is called a Bragg resonant wavelength $\lambda$, which is defined by the relationship $\lambda=2nd$, where n is an effective index in the fiber core and d is a grating periodicity. Other methods may also be used to prepare the refractive index periodic modulated grating.

In one embodiment, the central fiber core 112 comprises germanium dioxide ($GeO_2$) and fluorine (F) co-doped silica and has a diameter ranging from approximately 5 microns to approximately 9 microns. The periodic modulation may comprise an apodized, blazed, or blazed and apodized modulation, for example, for increasing guided core mode coupling to cladding modes by shedding guided mode field energy to the fiber cladding. In one embodiment, the refractive index periodic grating comprises a long-period fiber grating (LPG) structure 116 positioned around the fiber core 112.

In the illustrated embodiment, a fiber cladding 118 is circumferentially disposed about the fiber core 112 and, in one embodiment, has an outer diameter of approximately 125 microns and is made from pure silica. In one embodiment, the fiber cladding 118 is configured to act as a waveguide for light propagation through the fiber core 112. The broadband tunable light source 110 is positioned in light communication with the optical fiber cable and emits a near infrared light that propagates through the fiber core 112.

In the illustrated embodiment, a nanostructural multilayered sensing layer 120 is disposed about the fiber cladding 118 of the LPG structure 116. The sensing layer 120 may also be referred to as a coating. The sensing layer 120 is configured to effectively assist the coupling of the mode of the fiber cladding 118 to the fundamental mode of the fiber core 112 by a refractive index variation, an optical absorption change, a sensing material stress change, or a combination thereof, for example. The sensing layer 120 is sensitive and/or activated by interactions with certain gases that induces the refractive index variation, the absorption change, the sensing material stress change, or other change. For example, the sensing layer 120 may be sensitive to the hydrogen gas 52, the $CO_2$ gas 54, or other gases. In some embodiments, the fiber optic purity sensor 34 may include a first sensing layer 120 configured to enable detection of the level of hydrogen 52 in air 58, a second sensing layer configured to enable detection of the level of hydrogen 52 in $CO_2$ 54, and a third sensing layer configured to enable detection of the level of $CO_2$ 54 in air 58. More generally, the fiber optic purity sensor 34 may include a first sensing layer 120 configured to enable detection of the level of hydrogen 52, and a second sensing layer configured to enable detection of a second gas level. In one embodiment, the sensing layer 120 includes a multilayered nanostructural sensing film, which turns its ambient opaque minor-like surface into a more translucent surface upon hydride formation on the nanostructural multilayered sensing film upon exposure to the hydrogen gas 52. The formation of the hydride changes the cladding mode boundary and coupling efficiency so that the transmission wavelength and its power loss of the fiber grating-based hydrogen purity sensor 34 are modulated. The modulated signal then passes through the fiber optic cable 38 to the interrogator 36.

In a particular embodiment, the fiber gas hydrogen purity sensor 34 has a length along a longitudinal axis 114 of the optical fiber core 112 of approximately 10 mm to approximately 50 mm. The LPG structure 116 has a length along the longitudinal axis 114 of approximately 10 mm to approximately 30 mm with a cladding diameter of approximately 0.05 mm to approximately 0.125 mm. The LPG structure 116 has a modulation along the longitudinal axis 114 with a pitch size of approximately 0.1 microns to approximately 0.6 microns. The LPG structure 116 is configured to effectively shed fundamental mode energy to the modes of the fiber cladding 118 with apodized or blazed refractive index modulation profile. When the refractive index of the sensing material of the sensing layer 120 is lower than the fiber cladding 118, the modes of the fiber cladding 118 are guided by sensing material/cladding and fiber core interfaces. Partial light energy dissipates into the sensing material by an evanescent field while the cladding modes partially dissipate the energy into the sensing coating layer as radiation modes.

FIG. 6 is a flow chart of a process 150 that may be used by the control system 40 to operate an embodiment of the electrical generator 12. In a step 152, sensor data from at least one fiber optic sensor 34 disposed along the gas coolant path, such as the hydrogen coolant path 18, flowing through a rotary machine, such as the electrical generator 12, is obtained. The optical sensor may include not only the fiber optic purity sensor 34 but also a fiber optic pressure sensor, a fiber optic temperature sensor, a fiber optic flow rate sensor, and other fiber optic sensors. In a step 154, the optical sensor data is analyzed to determine a composition of the gas coolant. The composition of the gas coolant may include the purity of the gas (e.g., hydrogen) and the amounts of impurities (e.g., oxygen, nitrogen, etc.) in the gas coolant. In a step 156, the coolant purity is compared with a first threshold, which may be established at a level to help prevent corona discharges or to help increase the efficiency of the rotary machine, for example. The first threshold may be referred to as a "low-low" level. If the coolant purity is above the first threshold, the process 150 proceeds to a step 160, in which the coolant purity is compared with a second threshold, or "low" level. If the coolant purity is above the second threshold, the process 150 returns to the step 152 to obtain further sensor data. If the coolant purity is below the second threshold, then in a step 162, a portion of the gas coolant is purged and new gas coolant (e.g., hydrogen) is added to help increase the gas purity. In other words, a portion of the hydrogen coolant with a sensed level of hydrogen purity below the second threshold is removed and higher purity hydrogen coolant with a level of hydrogen purity substantially greater than the second threshold is added. The step 162 may be accomplished by the purity controller 43 initiating an appropriate control function. By purging a portion of the gas coolant, impurities in the purged gas coolant may be removed and displaced by the new gas coolant. From the step 162, the process 150 returns to the step 152 to obtain further sensor data.

Returning to the step 156, if the coolant purity is below the first threshold, the process 150 proceeds to a step 164, in which the gas coolant is purged from the rotary machine and a flame resistant gas (e.g., $CO_2$) is added to decrease the purity of the gas coolant. Thus, the flame resistant gas displaces the gas coolant in the step 164. Examples of the flame resistant gas include, but are not limited to, $CO_2$, nitrogen, argon, inert gases, noble gases, or any combination thereof. In a step 168, the purity of the gas coolant is compared with a third threshold, which may be established at a level to help ensure that most of the gas coolant has been removed from the rotary machine. For example, in some embodiments, the third threshold may be approximately 5 percent hydrogen in $CO_2$. If the purity of the gas coolant is greater than the second threshold, then the process 150 returns to the step 164 to continue purging the gas coolant with the flame resistant gas.

If the gas coolant purity is below the second threshold, then in a step 170, the flame resistant gas and any remaining gas coolant may be purged with air. After the gas coolant and the flame resistant gas are adequately purged from the rotary machine, the process 150 moves to a step 172, in which maintenance may be performed on the rotary machine to determine and repair any problems. After repairs are completed on the rotary machine, the process described above may be essentially performed in reverse to place the rotary machine back in service. Specifically, the flame resistant gas may displace the air in the rotary machine. Next, the gas coolant may displace the flame resistant gas until the purity of the gas coolant exceeds the second threshold. At that point, the rotary machine may be restarted.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system, comprising:
   an electrical generator comprising a stator, a rotor, and a gas coolant path through an interior of the electrical generator; and
   at least one fiber optic purity sensor configured to sense a gas purity of a flow of a gas coolant through the gas coolant path, wherein the at least one fiber optic purity sensor comprises:
   a fiber core;
   a refractive index periodic modulated grating structure positioned about the fiber core;
   a fiber cladding positioned around the refractive index periodic modulated grating structure; and
   a multilayered sensing film positioned about the fiber cladding, wherein the multilayered sensing film comprises:
   a modulated structure of multiple high refractive index and low refractive index material layers;
   a first coating configured to enable detection of a hydrogen level in air;
   a second coating configured to enable detection of a hydrogen level in carbon dioxide; and
   a third coating configured to enable detection of a carbon dioxide level in air.

2. The system of claim 1, wherein the gas coolant path comprises a rotor coolant path extending through the rotor, and the at least one fiber optic purity sensor comprises a rotor fiber optic purity sensor coupled to the rotor coolant path.

3. The system of claim 1, wherein the gas coolant path comprises a stator coolant path extending through the stator, and the at least one fiber optic purity sensor comprises a stator fiber optic purity sensor coupled to the stator coolant path.

4. The system of claim 1, wherein the gas coolant path comprises a bearing coolant path extending through a bearing system, and the at least one fiber optic purity sensor comprises a bearing fiber optic purity sensor coupled to the bearing coolant path.

5. The system of claim 1, comprising a control panel, wherein the at least one fiber optic purity sensor is disposed in the control panel, and wherein the gas coolant path comprises an external gas coolant line extending from the electrical generator to the control panel, and wherein the external gas coolant line is configured to carry a portion of the gas coolant from the electrical generator to the control panel.

6. The system of claim 5, wherein the control panel comprises:
   an interrogator configured to determine gas purity information based on a signal from the at least one fiber optic purity sensor; and
   a display configured to output the gas purity information.

7. The system of claim 6, comprising at least one of a fiber optic pressure sensor, a fiber optic temperature sensor, or a fiber optic flow rate sensor, wherein the interrogator is configured to determine at least one of a gas pressure, a gas temperature, or a gas flow rate based on signals from the at least one of the fiber optic pressure sensor, the fiber optic temperature sensor, or the fiber optic flow rate sensor, wherein the display is configured to output the at least one of the gas pressure, the gas temperature, or the gas flow rate.

8. The system of claim 1, wherein the gas coolant path comprises an internal gas coolant passage within the electrical generator, and the at least one fiber optic purity sensor is disposed along the internal gas coolant passage.

9. The system of claim 1 wherein the refractive index periodic modulated grating structure has a grating length between approximately 10 mm to 30 mm along a longitudinal axis of the fiber core.

10. The system of claim 1, wherein the at least one fiber optic purity sensor has a sensor length between approximately 10 mm to 50 mm along a longitudinal axis of the fiber core.

11. A system, comprising:
    a gas purity control system comprising a purity controller, and at least one fiber optic purity sensor configured to sense a gas purity, wherein the at least one fiber optic purity sensor comprises:
    a fiber core;
    a refractive index periodic modulated grating structure positioned about the fiber core;
    a fiber cladding positioned around the refractive index periodic modulated grating structure; and
    a multilayered sensing film positioned about the fiber cladding, wherein the multilayered sensing film comprises:
    a modulated structure of multiple high refractive index and low refractive index material layers;
    a first coating configured to enable detection of a hydrogen level; and
    a second coating configured to enable detection of a second gas level; and
    a rotary machine comprising an internal gas passage extending through an interior of the rotary machine, and the internal gas passage comprises the gas.

12. The system of claim 11, wherein the purity controller is configured to initiate a control function to increase the gas purity if a sensed level is below a threshold level of the gas purity.

13. The system of claim 11, wherein the at least one fiber optic purity sensor comprises a first fiber optic purity sensor configured to sense a first gas purity of a first region of a machine, and a second fiber optic purity sensor configured to sense a second gas purity of a second region of the machine.

14. A system, comprising:
    at least one fiber optic purity sensor configured to sense a gas purity of a gas coolant, wherein the at least one fiber optic purity sensor comprises a fiber core, a refractive index periodic modulated grating structure positioned about the fiber core, a fiber cladding positioned around the refractive index periodic modulated grating structure, and a multilayered sensing film positioned about the fiber cladding, wherein the multilayered sensing film comprises a modulated structure of multiple high refractive index and low refractive index material layers, and wherein the multilayered sensing film comprises a first coating configured to enable detection of a hydrogen level in air, a second coating configured to enable detection of a hydrogen level in carbon dioxide, and a third coating configured to enable detection of a carbon dioxide level in air; and a purity controller configured to initiate a control function to increase the gas purity if a sensed level is below a threshold level of the gas purity.

15. The system of claim 14, wherein the control function is configured to remove a portion of the gas coolant with the sensed level of gas purity, and the control function is configured to add higher purity gas coolant with a level of gas purity substantially greater than the threshold level.

16. The system of claim 14, comprising an electrical rotary machine having a gas coolant path, wherein the at least one fiber optic purity sensor is coupled to the gas coolant path.

* * * * *